United States Patent [19]

Kuwata et al.

[11] Patent Number: 6,117,420
[45] Date of Patent: Sep. 12, 2000

[54] HAIR-CARE TREATMENT TOILETRY COMPOSITION

[75] Inventors: Satoshi Kuwata; Motohiko Hirai, both of Gunma-ken, Japan

[73] Assignee: Shin-Etsu Chemical Co., Ltd., Tokyo, Japan

[21] Appl. No.: 09/188,098

[22] Filed: Nov. 9, 1998

[30] Foreign Application Priority Data

Nov. 12, 1997 [JP] Japan .................................. 9-310814

[51] Int. Cl.⁷ .................................................. A61K 7/06
[52] U.S. Cl. .................................. 424/70.121; 424/70.12
[58] Field of Search ............................. 424/70.12, 70.121

[56] References Cited

U.S. PATENT DOCUMENTS

| | | | |
|---|---|---|---|
| 5,196,187 | 3/1993 | Nicoll et al. .............................. | 424/70 |
| 5,362,485 | 11/1994 | Hayama et al. .......................... | 424/70 |
| 5,374,420 | 12/1994 | Gerstein . | |
| 5,756,112 | 5/1998 | Mackey .................................... | 424/402 |
| 5,925,341 | 7/1999 | Cervantes et al. ................... | 424/78.03 |
| 5,969,038 | 10/1999 | Fecht et al. .............................. | 524/837 |
| 6,007,801 | 12/1999 | Hoessel et al. . | |

FOREIGN PATENT DOCUMENTS 0 834 300   4/1998   European Pat. Off. .

*Primary Examiner*—Thurman K. Page
*Assistant Examiner*—P. McQueeney
*Attorney, Agent, or Firm*—Millen, White, Zelano and Branigan, P.C.

[57] ABSTRACT

Disclosed is a hair-care treatment toiletry composition, such as hair shampoo and hair rinse compositions, capable of imparting excellent smoothness and pliability as well as an adequate moisturized touch feeling to the hair treated therewith. The hair-care treatment toiletry composition contains, as the characteristic ingredient in addition to the usual ingredients acceptable as constituents of a hair-care treatment toiletry composition, a specified amount of a specific morpholino-modified diorganopolysiloxane, e.g., a dimethylpolysiloxane substituted by 3-morpholinopropyl groups for a part of the methyl groups as bonded to the silicon atoms in the organopolysiloxane molecules.

17 Claims, No Drawings

HAIR-CARE TREATMENT TOILETRY COMPOSITION

BACKGROUND OF THE INVENTION

The present invention relates to a novel hair-care treatment toiletry composition or, more particularly, to a toiletry composition for hair-care treatment capable of imparting excellent smoothness and pliability as well as adequate moisturized touch feeling to the hair treated therewith.

Needless to say, damages are sometimes unavoidable on hairs including mechanical damages due to brushing, combing and shampooing and physical and chemical damages due to sunlight, hot air by use of hair dryers and chemical reagents used in permanent-wave setting. It is conventional in order to reduce these damages on hairs that the hair is treated with a hair-care treatment toiletry composition formulated with an oily ingredient including vegetable oils such as camellia oil and olive oil, animal oils such as lanolin and beef tallow and mineral oils such as petrolatum and paraffin as well as various kinds of synthetic oils and the oily ingredient is compounded with a base hair-care treatment toiletry composition as such, in the form of an aqueous emulsion or in the form of a solution prepared by dissolving the same in an organic solvent.

In recent years, a variety of hair-care treatment toiletry compositions are proposed by formulating the composition, in place of the above mentioned various oily compounds, with an organopolysiloxane or a so-called silicone compound based on a discovery that a hair-care treatment toiletry composition containing a certain kind of silicone is capable of imparting improved glossiness, pliability, slipperiness and moisturized touch feeling to the hair treated with the composition. Some silicone compounds are already under practical applications.

For example, Japanese Patent Kokai 52-47923 discloses a hair treatment composition compounded with a dimethylpolysiloxane in combination with a diol compound or an aliphatic branched alcohol. Japanese Patent Kokai 55-136214 proposes a hair conditioner composition containing a polyorganosiloxane-polyoxyalkylene block copolymer in combination with hydrous or anhydrous ethyl alcohol.

The hair-care treatment compositions formulated with a dimethylpolysiloxane in general, however, have a serious disadvantage that, due to the susceptibility of a dimethylpolysiloxane to accumulation of static electric charges, the hair treated with the toiletry composition containing a dimethylpolysiloxane is liable to have deposition of dust particles. Further, when a dimethylpolysiloxane is contained in a water-base toiletry composition such as hair shampoos, hair rinses and hair conditioners, the stability of the water-base composition is sometimes decreased due to the strong hydrophobicity of the dimethylpolysiloxane. The polyorganosiloxane-polyoxyalkylene block copolymer as an adjuvant in a hair-care treatment toiletry composition is not fully effective in improving slipperiness of the hair treated with the composition.

In view of the above described disadvantages in the hair treatment compositions formulated with conventional silicone materials, proposals were made for cationic hair treatment compositions including, for example, a hair treatment composition comprising an aminoalkyl methyl polysiloxane, a cationic surface active agent and a water-base carrier as disclosed in Japanese Patent Kokai 56-45406, a toiletry composition containing an organopolysiloxane having cation-active nitrogen-containing groups as disclosed in Japanese Patent Kokai 55-66506 and a hair treatment composition containing an organopolysiloxane having amino groups and polyoxyalkylene groups in combination as disclosed in Japanese Patent Publication 6-96499.

The inventors, on the other hand, have developed a hair treatment composition formulated with a specific amino-modified organopolysiloxane having block units of polyoxyalkylene groups, which is disclosed in Japanese Patent Kokai 9-194335, but the improvement accomplished thereby is still not quite satisfactory though not ineffective.

SUMMARY OF THE INVENTION

The present invention accordingly has an object to provide a novel and improved hair-care treatment toiletry composition capable of imparting excellent smoothness, pliability, moisturized touch feeling and glossiness to the hair treated therewith by overcoming the above described disadvantages and problems in the conventional hair-care treatment toiletry compositions formulated with a silicone material.

Thus, the hair-care treatment toiletry composition provided by the present invention is a uniform mixture which comprises:

(a) from 0.01 to 10% by weight of a morpholino-modified organopolysiloxane represented by the average structural formula

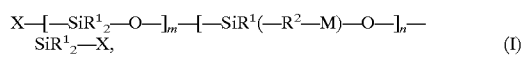

$$X-[-SiR^1{}_2-O-]_m-[-SiR^1(-R^2-M)-O-]_n-SiR^1{}_2-X, \qquad (I)$$

in which $R^1$ is a monovalent hydrocarbon group having 1 to 20 carbon atoms, $R^2$ is a divalent hydrocarbon group having 1 to 6 carbon atoms, M is a morpholino group, X is $R^1$ or a group of the formula $OR^3$, $R^3$ being a hydrogen atom or a monovalent hydrocarbon group having 1 to 6 carbon atoms, the subscript m is a positive number in the range from 10 to 10000 and the subscript n is a positive number in the range from 1 to 100 with the proviso that the ratio m:n is in the range from 10 to 1000 or, preferably, from 20 to 100; and (b) the balance of ingredients acceptable as the base constituents of a hair-care treatment toiletry composition.

DETAILED DESCRIPTION OF THE PREFERRED EMBODIMENTS

The above defined novel hair-care treatment toiletry composition of the invention, which has been developed as a result of the extensive investigations undertaken by the inventors to solve the problems in the prior art, is characterized by the formulation of a very specific and unique organopolysiloxane compound as the component (a). Namely, the inventors have discovered that a morpholino-modified organopolysiloxane has good adsorptivity on hairs so that the hair treated with a toiletry composition containing such a morpholino-modified organopolysiloxane can be imparted with excellent smoothness and pliability as well as adequate moisturized touch feeling.

The most characteristic ingredient in the inventive hair-care treatment toiletry composition is the component (a) which is a diorganopolysiloxane having, in a molecule, at least one morpholino-modified organosiloxane unit. In the general formula (I) representing the morpholino-modified organopolysiloxane, $R^1$ is a monovalent hydrocarbon group having 1 to 20 carbon atoms exemplified by alkyl groups such as methyl, ethyl, propyl, butyl, pentyl, hexyl, heptyl, octyl, decyl, dodecyl, tetradecyl and octadecyl groups, alkenyl groups such as vinyl and allyl groups, cycloalkyl groups such as cyclopentyl and cyclohexyl groups and aryl groups such as phenyl, tolyl and naphthyl groups. These hydrocarbon groups can be substituted by halogen atoms for a part or all of the hydrogen atoms therein. It is particularly preferable that at least 90% by moles of the groups denoted by $R^1$ in a molecule are methyl groups, the balance, if any, being phenyl and/or vinyl groups.

The group denoted by $R^2$ in the general formula (1) is a divalent hydrocarbon group having 1 to 6 carbon atoms, which is a linking group between a morpholino group M and a silicon atom Si in the organopolysiloxane molecule. The divalent hydrocarbon group is preferably an alkylene group exemplified by methylene, dimethylene, trimethylene, tetramethylene, pentamethylene and hexamethylene groups, of which trimethylene group is more preferable.

The group denoted by X at each molecular chain end of the organopolysiloxane molecules represented by the general formula (I) can be the same as $R^1$ defined above or a group expressed by the formula $OR^3$, in which $R^3$ is a hydrogen atom or a monovalent hydrocarbon group or, preferably, alkyl group having 1 to 6 carbon atoms including methyl, ethyl, propyl, butyl, pentyl and hexyl groups. When $R^3$ is an alkyl group, the methyl group is particularly preferable as the group $R^3$.

The subscript m in the general formula (I), which gives the average number of the diorganosiloxane units —$SiR^1_2$—O— in the molecules of the organopolysiloxane as the component (a), is in the range from 10 to 10000 or, preferably, from 100 to 1000. When the value of the subscript m is too small, the hairs treated with the hair-care treatment toiletry composition formulated with such an organopolysiloxane cannot be imparted with fully improved slipperiness. When the value of the subscript m is too large, on the other hand, difficulties are encountered in uniformly compounding the organopolysiloxane with other ingredients due to a decrease in the compatibility as a consequence of the excessively large molecular weight of the organopolysiloxane.

The subscript n in the general formula (I), which gives the average number of the morpholino-containing diorganosiloxane units of the formula —$SiR^1(R^2—M)$—O— in the molecules of the organopolysiloxane as the component (a), is in the range from 1 to 100 or, preferably, from 5 to 50. When the value of the subscript n is too small, the hairs treated with the hair-care treatment toiletry composition formulated with such an organopolysiloxane cannot be imparted with an adequately moisturized touch feeling due to deficiency in the content of the morpholino groups. When the value of the subscript n is too large, on the other hand, the hairs treated with the hair-care toiletry composition formulated with such an organopolysiloxane cannot be imparted with fully improved slipperiness. The ratio of the subscripts m:n should be in the range from 10 to 1000 or, preferably, from 20 to 100 in order to ensure an adequate content of the morpholino groups in the organopolysiloxane.

The morpholino-modified organopolysiloxane represented by the general formula (I) can easily be prepared according to a known synthetic procedure disclosed, for example, in Japanese Patent Kokai 58-76578 and elsewhere. For example, a hydrolysis-condensation product of 3-morpholinopropyl methyl dimethoxy silane of the formula $(MeO)_2SiMe(CH_2CH_2CH_2—M)$, in which Me is a methyl group and M is a morpholino group, is admixed with a cyclic diorganosiloxane oligomer, such as octamethyl cyclotetrasiloxane, and hexamethyl disiloxane and the organosiloxane mixture is further admixed with an alkali catalyst, such as an alkaline silanolate, and heated to effect the siloxane rearrangement equilibration reaction. Alternatively, the morpholino-modified organopolysiloxane can be prepared by the dehydrohalogenation condensation reaction between morpholine and an organopolysiloxane having silicon-bonded halogenoalkyl groups such as chloromethyl and chloropropyl groups.

The amount of the morpholino-modified organopolysiloxane as the component (a) in the inventive hair-care treatment toiletry composition is in the range from 0.01 to 10% by weight or, preferably, from 0.1 to 5% by weight depending on the types of the toiletry composition and the desired degree of improvement by the formulation with the component (a). When the amount of the morpholino-modified organopolysiloxane is too small, the desired effect such as the slipperiness of the hair treated with the hare-care treatment toiletry composition cannot be fully obtained as a matter of course while, when the amount thereof is too large, tackiness sometimes appears on the hair treated with the hair-care toiletry composition containing a too large amount of the morpholino-modified organopolysiloxane.

The component (b) in the inventive toiletry composition includes various materials acceptable as the constituents of a hair-care treatment toiletry composition known per se by those skilled in the art of toiletry and cosmetic preparations and is selected depending on the particular types of the hair-care treatment toiletry compositions. Namely, the component (b) is selected from the group consisting of water and ethyl alcohol as the dispersing medium, oily and waxy materials, surface active agents, polyhydric alcohols, thickening agents, powder materials, perfumes, preservatives and others. In compounding the toiletry composition with the component (a), the organopolysiloxane is directly emulsified in an aqueous medium together with the other ingredients as the component (b) such as an oily material and surface active agent. Alternatively, the organopolysiloxane is added to and dissolved or emulsified in an alcoholic or aqueous solution or emulsion of the other ingredients. Further, the organopolysiloxane can be blended and kneaded with other oily or waxy ingredients and powder ingredients.

The surface active agent mentioned above, which is an essential ingredient in the hair-care treatment toiletry compositions of most types, includes non-ionic, anionic, cationic and amphoteric surface active agents exemplified by fatty acid soaps, alkylbenzene sulfonates, alkyl sulfates, alkyl ether sulfates, monoglyceride sulfates, alkyl phosphates, methyl taurate, fatty acid alkanolamides and the like. These surface active agents can be used in combination of two kinds or more, if they are compatible each with the others.

When the inventive hair-care treatment toiletry composition is a shampoo composition for human hairs or for animal hairs, it is advantageous that the shampoo composition contains, as one of the ingredients as the component (b), an aliphatic alcohol or an aliphatic alcohol ethoxylate or, in particular, ethoxylates derived from lauryl alcohol or myristyl alcohol or salts thereof. Such a salt is exemplified by sodium lauryl sulfate, sodium lauryl ether sulfate, ammonium lauryl sulfate, triethanolamine lauryl sulfate, monoethanolamine lauryl sulfate and disodium lauryl ethoxy sulfosuccinate.

The hair-care treatment toiletry composition of the invention can be prepared in the form of an aqueous solution, aqueous emulsion, aerosol, solid cake, paste, powder and others depending on the particularly intended application of the composition.

The application forms of the inventive toiletry composition include hair shampoos, hair rinses, aftershampoos, hair conditioners, hair-set lotions, blow-styling lotions, pre-shampoo treatments, hair sprays, hair-styling gels, hair dyes, hair bleaches, permanent wave setting agents, hair liquids, hair tonics and the like.

In the following, the hair-care treatment toiletry composition of the invention is illustrated in more detail by way of Examples and Comparative Examples as preceded by a description of the synthetic procedure of the morpholino-modified organopolysiloxane as the component (a). In the following description, the terms of "%" and "parts" always refer to "% by weight" and "parts by weight", respectively, and the values of viscosity are all those obtained by the measurement at 25° C.

Synthesis 1.

Into a glass flask of 1 liter capacity with a separable cover equipped with a stirrer, thermometer, reflux condenser and gas inlet tube were introduced 690 g of octamethyl cyclotetrasiloxane, 44 g of dodecamethyl pentasiloxane and 90 g of a hydrolysis-condensation product of 3-morpholinopropyl methyl dimethoxy silane to form a reaction mixture which was heated under agitation with introduction of nitrogen gas to reach a temperature of 110° C. The reaction mixture kept at this temperature was admixed with 0.5 g of tetrabutylphosphonium hydroxide as an alkaline catalyst and further agitated for 5 hours at the same temperature to effect the siloxane rearrangement equilibration reaction followed by a temperature elevation up to 150° C. and agitation for an additional 1 hour to complete the reaction. After cooling, the reaction mixture was subjected to a stripping treatment of volatile materials at 140° C. under reduced pressure to obtain 740 g of a clear, pale yellow liquid product having a viscosity of 600 centipoise and an amine equivalent of 1800 g/mole. This liquid product, referred to as the organopolysiloxane 1 hereinafter, could be expressed by the average structural formula

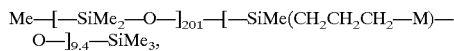

in which Me is a methyl group and M is a morpholino group.

Synthesis 2.

The synthetic procedure was substantially the same as in Synthesis 1 described above except that the reaction mixture was prepared from 670 g of octamethyl cyclotetrasiloxane, 16 g of dodecamethyl pentasiloxane and 33 g of the hydrolysis-condensation product of 3-morpholinopropyl methyl dimethoxy silane to obtain 650 g of a clear, pale yellow liquid product having a viscosity of 9200 centipoise and an amine equivalent of 4300 g/mole. This liquid product, referred to as the organopolysiloxane 2 hereinafter, could be expressed by the average structural formula

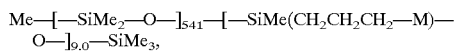

in which Me is a methyl group and M is a morpholino group.

EXAMPLE 1

A hair shampoo composition was prepared by uniformly mixing the following ingredients (1) to (6) by using a propeller-blade stirrer unit.

| | |
|---|---|
| (1) Sodium polyoxyethylene (3 moles EO addition) lauryl sulfate | 16% |
| (2) Lauryl sulfuric acid diethanolamide | 4% |

-continued

| | |
|---|---|
| (3) Organopolysiloxane 1 | 2% |
| (4) Propyleneglycol | 2% |
| (5) Methyl p-oxybenzoate | 0.1% |
| (6) Purified water | (balance to 100%) |

The thus prepared shampoo composition was subjected to an organoleptic evaluation test by 10 panel members, each of whom shampooed his or her hair with the shampoo composition followed by drying by using a hair dryer to report that the hair exhibited excellent smoothness in combing and gave a touch feeling of excellent pliability and adequately moisturized condition.

COMPARATIVE EXAMPLE 1

The formulation of the comparative hair shampoo composition was just the same as in Example 1 described above excepting for the replacement of the organopolysiloxane 1 used in Example 1 with the same amount of a dimethylpolysiloxane oil (KF 96, a product by Shin-Etsu Chemical Co.) having a viscosity of 500 centipoise. The result of the organoleptic evaluation test of the comparative shampoo composition undertaken in the same manner as in Example 1 reported by the panel members was that their hairs were apparently in an inferior condition as compared with Example 1 relative to the smoothness in combing and in the touch feeling of pliability and moisturized condition.

EXAMPLE 2

A hair rinse composition was prepared in the following formulation including the ingredients (1) to (7).

| | |
|---|---|
| Stearyl trimethyl ammonium chloride | 1% |
| (2) Cetanol | 2% |
| (3) Organopolysiloxane 2 | 2% |
| (4) Propyleneglycol | 5% |
| (5) Hydroxyethyl cellulose | 1% |
| (6) Methyl p-oxybenzoate | 0.1% |
| (7) Purified water | (balance to 100%) |

In the first place, the ingredients (5) and (7) were mixed and heated at 70° C. to form a solution, into which a melt of the ingredients (1), (2), (3) and (4) at 70° C. was introduced under agitation. After cooling to 50° C., the blend was admixed with the ingredient (6) and then cooled to room temperature to give a hair rinse composition.

The thus prepared hair rinse composition was subjected to an organoleptic evaluation test by 10 panel members, each of whom shampooed his or her hair by using a commercial shampoo product and rinsed the hair with the rinse composition and water followed by drying by using a hair dryer. The result reported by them was that the hair exhibited excellent smoothness in combing and gave a touch feeling of excellent pliability and adequately moisturized condition.

COMPARATIVE EXAMPLE 2

The formulation of the comparative hair rinse composition was just the same as in Example 2 described above excepting for the replacement of the organopolysiloxane 2 used in Example 2 with the same amount of a dimethylpolysiloxane oil (KF 96H, a product by Shin-Etsu Chemical Co.) having a viscosity of 10000 centipoise. The result of the organoleptic evaluation test of the hair rinse composition undertaken in the same manner as in Example 2 reported by the panel members was that their hairs were apparently in an inferior condition as compared with Example 2 relative to the smoothness in combing and in the touch feeling of pliability and moisturized condition.

What is claimed is:

1. A hair-care treatment toiletry composition, as a uniform mixture, which comprises a uniform aqueous emulsion of:

(a) from 0.01 to 10% by weight of a morpholino-modified organopolysiloxane represented by the average general formula

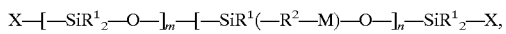

in which $R^1$ is a monovalent hydrocarbon group having 1 to 20 carbon atoms, $R^2$ is a divalent hydrocarbon group having 1 to 6 carbon atoms, M is a morpholino group, X is $R^1$ or a group of the formula $OR^3$, $R^3$ being a hydrogen atom or a monovalent hydrocarbon group having 1 to 6 carbon atoms, the subscript m is a number in the range from 10 to 10000 and the subscript n is a number in the range from 1 to 100; and (b) the balance of ingredients acceptable as the base constituents of a hair-care treatment toiletry composition.

2. The hair-care treatment toiletry composition as claimed in claim 1 in which the monovalent hydrocarbon group denoted by $R^1$ is selected from the group consisting of alkyl groups, alkenyl groups, cycloalkyl groups and aryl groups.

3. The hair-care treatment toiletry composition as claimed in claim 1 in which at least 90% by moles of the monovalent hydrocarbon groups denoted by $R^1$ are methyl groups.

4. The hair-care treatment toiletry composition as claimed in claim 1 in which the group denoted by X is a methyl group.

5. The hair-care treatment toiletry composition as claimed in claim 1 in which the subscript m is a number in the range from 100 to 1000.

6. The hair-care treatment toiletry composition as claimed in claim 1 in which the subscript n is a number in the range from 5 to 50.

7. The hair-care treatment toiletry composition as claimed in claim 1 in which the group denoted by $R^2$ is a trimethylene group.

8. The hair-care treatment toiletry composition as claimed in claim 1 in which the amount of the component (a) is in the range from 0.1 to 5% by weight.

9. The hair-care treatment toiletry composition as claimed in claim 1 in which the ratio of the subscripts m and n in the general formula representing the component (a), m:n, is in the range from 10:1000.

10. The hair-care treatment toiletry composition as claimed in claim 9 in which the ratio of m:n is in the range from 20:100.

11. The composition of claim 1, wherein the balance of ingredients, (b), includes those selected from the group consisting of water, ethyl alcohol, oily or waxy materials, surface active agents, polyhydric alcohols, thickening agents, powder materials, perfumes, preservatives and combinations thereof.

12. The composition of claim 1, wherein the balance of ingredients, (b), includes a surface active agent.

13. The composition of claim 12, wherein the surface active agent is selected from the group consisting of fatty acid soaps, alkylbenzene sulfonates, alkyl sulfates, alkyl ether sulfates, monoglyceride sulfates, alkyl phosphates, methyl taurate, fatty acid alkanolamides and combinations thereof.

14. The composition of claim 1, wherein the composition is in the form of a hair shampoo.

15. The composition of claim 14, wherein the composition further comprises an aliphatic alcohol, aliphatic alcohol ethoxylate or salt thereof.

16. The composition of claim 1, wherein the composition is in the form of a hair rinse, an aftershampoo, a hair conditioner, a hair-set lotion, a blow-styling lotion, a pre-shampoo treatment, a hair spray, a hair-styling gel, a hair dye, a hair bleach, a permanent wave setting agent or a hair tonic.

17. The composition of claim 1, wherein the amount of component (a) in the composition is from 0.1 to 5% by weight.

* * * * *